(12) United States Patent
Meyer et al.

(10) Patent No.: US 10,753,996 B2
(45) Date of Patent: Aug. 25, 2020

(54) METHOD AND MAGNETIC RESONANCE APPARATUS WHEREIN STORED DATA ACQUISITION PROTOCOLS ARE AUTOMATICALLY CONFORMED TO A CURRENT EQUIPMENT VERSION

(71) Applicant: Siemens Healthcare GmbH, Erlangen (DE)

(72) Inventors: Stefan Meyer, Langensendelbach (DE); Stefan Schor, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 103 days.

(21) Appl. No.: 15/959,939

(22) Filed: Apr. 23, 2018

(65) Prior Publication Data
US 2018/0306883 A1 Oct. 25, 2018

(30) Foreign Application Priority Data
Apr. 24, 2017 (EP) ..................... 17167787

(51) Int. Cl.
*G01R 33/56* (2006.01)
*G01R 33/28* (2006.01)
(Continued)

(52) U.S. Cl.
CPC .......... *G01R 33/5608* (2013.01); *A61B 6/545* (2013.01); *G01R 33/283* (2013.01);
(Continued)

(58) Field of Classification Search
CPC .............. G01R 33/5608; G01R 33/283; G01R 33/543; A61B 6/545; G16H 30/20; G16H 30/40; G16H 40/63; G16H 40/40
See application file for complete search history.

(56) References Cited

U.S. PATENT DOCUMENTS 6,353,445 B1 * 3/2002 Babula ................ A61B 5/0002
715/733
6,377,162 B1 * 4/2002 Delestienne ........... G16H 40/40
340/286.07
(Continued)

FOREIGN PATENT DOCUMENTS

DE 102010034430 A1 2/2012

OTHER PUBLICATIONS

Office Action dated Sep. 26, 2019 for German patent Application No. 17167787.5.

*Primary Examiner* — Dixomara Vargas
(74) *Attorney, Agent, or Firm* — Schiff Hardin LLP

(57) ABSTRACT

In a medical imaging apparatus and method for operation thereof, data acquisition protocols are stored, each containing data acquisition parameters of the medical imaging apparatus that define a data acquisition operation. In the event of an update, which changes the possible setting scope for data acquisition parameters, of at least one software and/or hardware component of the medical imaging apparatus to a current equipment version, and/or in the event of the input of a data acquisition protocol not defined for the current equipment version, a set of rules is applied to all protocols not defined for the current equipment version. The rules include at least one adaptation rule for at least one data acquisition parameter, which rule, when applicable, increases at least one quality measure for image data recorded using the data acquisition protocol to which the adaptation rule is applied.

16 Claims, 2 Drawing Sheets

(51) Int. Cl.
   *A61B 6/00*      (2006.01)
   *G16H 40/63*     (2018.01)
   *G01R 33/54*     (2006.01)
   *G16H 30/20*     (2018.01)
   *G16H 40/40*     (2018.01)
   *G16H 30/40*     (2018.01)
   *A61B 6/03*      (2006.01)
   *A61B 5/055*     (2006.01)

(52) U.S. Cl.
   CPC .......... *G01R 33/543* (2013.01); *G16H 30/20* (2018.01); *G16H 30/40* (2018.01); *G16H 40/40* (2018.01); *G16H 40/63* (2018.01); *A61B 5/055* (2013.01); *A61B 6/032* (2013.01)

(56) References Cited

U.S. PATENT DOCUMENTS

| | | | | |
|---|---|---|---|---|
| 6,381,557 | B1 * | 4/2002 | Babula | G16H 40/40 |
| | | | | 702/183 |
| 6,434,572 | B2 * | 8/2002 | Derzay | G06F 19/3418 |
| 6,516,324 | B1 * | 2/2003 | Jones | G06F 19/321 |
| | | | | 707/805 |
| 6,578,002 | B1 * | 6/2003 | Derzay | G06F 19/3418 |
| | | | | 705/2 |
| 6,598,011 | B1 * | 7/2003 | Howards Koritzinsky | |
| | | | | G06F 19/321 |
| | | | | 702/185 |
| 6,738,798 | B1 * | 5/2004 | Ploetz | A61B 6/56 |
| | | | | 345/581 |
| 6,832,199 | B1 * | 12/2004 | Kucek | A61B 5/0002 |
| | | | | 705/2 |
| 7,127,499 | B1 * | 10/2006 | Accardi | G16H 40/20 |
| | | | | 709/219 |
| 7,263,710 | B1 * | 8/2007 | Hummel, Jr. | G06F 19/324 |
| | | | | 725/86 |
| 7,770,164 | B2 * | 8/2010 | Schuelein | G06F 8/65 |
| | | | | 600/410 |
| 8,868,716 | B2 * | 10/2014 | Muralidharan | G06F 19/321 |
| | | | | 709/224 |
| 9,724,534 | B2 * | 8/2017 | Jacobson | A61N 2/02 |
| 9,821,169 | B2 * | 11/2017 | Jacobson | A61N 2/02 |
| 2002/0004798 | A1 * | 1/2002 | Babula | G06F 19/00 |
| 2005/0197864 | A1 | 9/2005 | Koritzinsky et al. | |
| 2006/0004870 | A1 * | 1/2006 | Pomeroy | G06F 19/3418 |
| 2006/0195564 | A1 * | 8/2006 | Accardi | G16H 40/20 |
| | | | | 709/223 |
| 2006/0271925 | A1 * | 11/2006 | Schuelein | G06F 8/65 |
| | | | | 717/168 |
| 2010/0057655 | A1 * | 3/2010 | Jacobson | G06F 19/325 |
| | | | | 706/45 |
| 2012/0041909 | A1 | 2/2012 | Glaser-Seidnitzer et al. | |
| 2013/0023753 | A1 * | 1/2013 | Kawamura | A61B 5/055 |
| | | | | 600/410 |
| 2013/0311472 | A1 * | 11/2013 | Cohen-Solal | G06F 19/321 |
| | | | | 707/737 |
| 2015/0091569 | A1 * | 4/2015 | Shinoda | A61B 5/055 |
| | | | | 324/309 |
| 2016/0045182 | A1 | 2/2016 | Stevens et al. | |
| 2016/0345928 | A1 * | 12/2016 | Jung | A61B 6/4464 |
| 2016/0350480 | A1 * | 12/2016 | Gerdeman | G16H 30/20 |
| 2017/0291039 | A1 * | 10/2017 | Jacobson | G16H 40/63 |
| 2017/0350878 | A1 * | 12/2017 | Holmes | G01N 21/07 |
| 2018/0060486 | A1 * | 3/2018 | Keil | G06F 19/32 |
| 2018/0068070 | A1 * | 3/2018 | Keil | A61B 6/54 |
| 2018/0144823 | A1 * | 5/2018 | Raman | G16H 40/67 |
| 2018/0306883 | A1 * | 10/2018 | Meyer | G16H 40/40 |
| 2018/0330818 | A1 * | 11/2018 | Hsieh | G16H 40/60 |
| 2019/0005195 | A1 * | 1/2019 | Peterson | G16H 50/30 |
| 2019/0354882 | A1 * | 11/2019 | Sharma | G06N 20/00 |

* cited by examiner

METHOD AND MAGNETIC RESONANCE APPARATUS WHEREIN STORED DATA ACQUISITION PROTOCOLS ARE AUTOMATICALLY CONFORMED TO A CURRENT EQUIPMENT VERSION

BACKGROUND OF THE INVENTION

Field of the Invention

The invention concerns a method for operating a medical imaging apparatus, especially a magnetic resonance apparatus, which has a memory for data acquisition protocols that contain a number of data acquisition parameters of the medical imaging apparatus and which define a data acquisition procedure. Additionally the invention concerns a medical imaging apparatus, and an electronically readable data storage medium that implement such a method.

Description of the Prior Art

Image data acquisition facilities with different modalities are employed frequently in the context of medical technology for diagnostic imaging. With the large number of diagnostic tasks, the complexity of setting the image data acquisition facilities also increases. Accordingly, image data acquisition facilities have a large number of setting options. This means that different values can be specified and/or changed by the user for a large number of data acquisition parameters that define a data acquisition procedure. In this regard the entirety of all data acquisition parameters that influence or respectively configure the imaging measurement can be saved in a memory of the medical imaging apparatus in the form of a data acquisition protocol (set of data acquisition parameters). Particular data acquisition protocols can already be made available to users by the manufacturer of the imaging apparatus, but image data acquisition facilities usually also have an input unit through which data acquisition protocols can be defined—by setting values for the data acquisition parameters—and saved in the memory by the user.

Image data acquisition facilities can be updated and/or expanded both with respect to hardware and with respect to software. For example, a new hardware component can be added that offers new data acquisition parameters and/or expands the possible setting scope for existing data acquisition parameters. Software components can be correspondingly added and/or updated, for example in the form of a software package. Overall the entirety of currently available hardware components and also the versions of the currently available software components can be designated as the current equipment version of the medical imaging apparatus. Updates with respect to the software components not only involve more current versions of software components that are already present, but also the acquisition of new licenses and therefore access to new software components.

If the current equipment version changes, it may be the case that data acquisition protocols currently present and stored in the memory are no longer executable, since they are not consistent with the current equipment version. For example, particular values for data acquisition parameters or even the data acquisition parameters as such may no longer be available. Combinations of values for data acquisition parameters may also no longer be permissible in a more current equipment version in some circumstances. A known approach is consequently to implement a consistency check for data acquisition protocols that are present in the memory in which they can be converted for the new, current equipment version, especially by removing setting options that no longer exist and/or data acquisition parameter combinations that are no longer permissible, and/or by converting changed data acquisition parameters to a new format. The data acquisition protocols thus can continue to be used in the current equipment version also. If a data acquisition protocol is consistent, then it is naturally unnecessary to change anything.

A similar procedure can be adopted if a data acquisition protocol is received from another medical imaging apparatus, for example via a server or an Internet portal through which data acquisition protocols are exchanged. Incoming data acquisition protocols of this type, which are defined for a different equipment version, can likewise be processed by the consistency check in order to generate compatibility.

In changing the equipment version however, it may occur, both in the case of an expansion of the possible setting scope and in the case of a reduction in the possible setting scope, that other combinations of values for data acquisition parameters, or completely new values for data acquisition parameters, prove more favorable in terms of the data acquisition goals to be achieved. If a user would like to use new data acquisition parameters and/or options for data acquisition parameters therefore, the user needs to manually adapt every data acquisition protocol, especially those that are self-defined, in the protocol database. Since it would not be used for several thousand protocols can to be stored in memories, an enormously large manual effort is needed. This manual effort also occurs when a data acquisition protocol defined for another equipment version is downloaded, for example via an Internet portal, and saved in the memory.

It has been suggested in the prior art that data acquisition protocols predefined by the manufacturer already be adapted by the manufacturer and be included in the scope of supply and/or at least made available in the event of an update of the equipment version of the medical imaging apparatus. This still does not reduce the effort to be carried out manually for data acquisition protocols defined by the user and saved individually in the memory.

SUMMARY OF THE INVENTION

An object of the invention is to provide a way that can be implemented with little effort to improve the quality of image data and/or the data acquisition of image data, by optimizing data acquisition protocols.

This object is achieved according to the invention in a method of the general type described above, but wherein, in the event of an update that changes the possible setting scope for data acquisition parameters of at least one software and/or hardware component of the medical imaging apparatus to a current equipment version, and/or in the event of the input of a data acquisition protocol not defined for the current equipment version, a set of rules is applied to all protocols not defined for the current equipment version. These rules include at least one adaptation rule for at least one data acquisition parameter, which when applicable, increases at least one quality measure for medical image data acquired using the data acquisition protocol to which the adaptation rule is applied.

The invention therefore applies a set of rules in a control computer of the medical imaging apparatus to data acquisition protocols not defined for the current equipment version, in order to be able to optimize them in terms of the quality measure. An optimization of data acquisition protocols with the use of a rule-based system is therefore implemented. A set of rules is defined, with adaptation rules with which the values of data acquisition parameters can be analyzed and where appropriate optimized. An automatic adaptation at least of user-created and/or imported data acquisition protocols to a current equipment version is therefore possible by this procedure so that manual adaptation is avoided. Possible optimizations are made available by the system. In the set of rules, knowledge about the best possible image quality or data acquisition quality, respectively, is mapped by the adaptation rules which are applied during the optimization of the data acquisition protocols.

The implementation of the method thus changes the contents of the memory, and thus changes the state of the medical imaging apparatus by putting the medical imaging apparatus in a state that conforms the medical imaging apparatus to the update or to the receipt of the data acquisition protocol that is not defined by the current equipment version of the medical imaging apparatus.

This is advantageous both after a hardware and/or software update, and especially also a license change, as well as in the context of importing data acquisition protocols from image data acquisition facilities with a different equipment version. Since clinics and radiology centers are tending to become ever larger and can therefore have multiple imaging image data acquisition facilities, exchanging data acquisition protocols between individual image data acquisition facilities will become ever more important. In the absence of optimal adaptation to the equipment version of the importing medical imaging apparatus however, the exchange would be of only minor benefit to the corresponding medical technology facilities since otherwise a very great deal of manual work would still be necessary. An exchange of data acquisition protocols can naturally also refer to exchange platforms operating beyond facility level, for example Internet platforms.

Even though many of the examples described herein refer to a magnetic resonance facility as the medical imaging apparatus, where dependencies between data acquisition parameters and complexity of the programming of data acquisition operations is generally very high, and therefore the inventive method can be applied especially advantageously, the method can also be applied to other typical image data acquisition facilities capable of using a large number of data acquisition protocols, for example computed tomography systems.

In an embodiment of the present invention, prior to application of the set of rules, a conversion algorithm is applied that generates compatibility, with the current equipment version, of the data acquisition protocols not defined for the current equipment version. A consistency check is therefore implemented initially where, in the case of data acquisition protocols that are not consistent with the current equipment version, a conversion takes place initially so as to produce compatibility with the current equipment version, but without undertaking optimizations in terms of the quality measure. In the context of generating compatibility for example, the removal of setting options no longer in existence and/or data acquisition parameter combinations that are no longer permissible, and/or a conversion to a new data format, can be carried out. An optimization using the set of rules can then follow, where appropriate on a user-selectable basis, after the consistency check and where appropriate generation of consistency.

In another embodiment of the present invention, a measure describing the image quality and/or a reduction in the data acquisition duration in the presence of at least constant image quality is used as a quality measure. It is preferable in this regard to employ a measure relating directly to the image quality. Suitable quality measures are known from the state of the art that can also differ according to the data acquisition goal of the data acquisition protocol to be optimized, for example measures relating to structures being readily identifiable (contrast) can be used as well as measures aimed at good homogeneousness, measures evaluating noise components, etc.

In another embodiment of the present invention, data acquisition parameters to be adapted, of a data acquisition protocol to be adapted, on the basis of an adaptation rule are initially displayed to a user as a suggestion and only adapted to the suggested values following a confirmatory user input. The user thus can cause possible optimizations of the medical imaging apparatus to be implemented in the control computer of the medical imaging apparatus, and confirm them after checking, if the user does not want a fully automatic setting. The new values for the data acquisition parameters are therefore presented to the user so that the user can confirm or reject them. Advantageously, a display of supporting information can be effected, for example showing a difference in the quality measure with and without adaptation and/or motivation information deposited in the adaptation rule. This makes it simpler for the user to understand the background of the suggestion.

Preferably the data acquisition protocols to be stored in the memory are data acquisition protocols predefined by the manufacturer, wherein in the event of an update, which changes the possible setting scope for data acquisition parameters, of at least one software and/or hardware component of the medical imaging apparatus to a current equipment version, the user protocols predefined by the manufacturer are also updated. This means that along with the update containing the software and/or hardware component, data acquisition protocols that are already adapted and optimized are also supplied by the manufacturer, which protocols need not be converted or optimized further therefore, but instead already make optimal use of the options provided by the update. This reduces the effort at the medical imaging apparatus.

As already mentioned, provision can also be made that the update comprises a change to a license for software components, by means of which setting options are added and/or omitted. It is therefore also possible to respond to a license change of this type by optimizing at least the user-defined data acquisition protocols, so that regardless of whether setting options are being added or omitted, the best image quality is always made available for the user.

In another embodiment, an adaptation rule includes at least one condition to be fulfilled for application of the adaptation rule and an adaptation measure to be implemented upon fulfillment of the at least one condition. The at least one condition evaluates the current equipment version and/or at least one of the data acquisition parameters. Conditions can therefore be logical queries about particular information, for example. Thus it is possible to check whether a current value of a data acquisition parameter is larger or smaller than a constant, corresponds exactly to a constant, and/or does not correspond to that constant, which can naturally also be transposed to combinations of data acquisition parameters. Furthermore it also possible to check with reference to software components whether particular licenses are available and/or, with regard to software components and hardware components, whether the corresponding component is actually present and capable of operating. Adaptation measures contain the data acquisition parameter to be adapted and the new value, which does not necessarily have to be a constant, but instead can also be produced as a function of other data acquisition parameters.

During an optimization of a data acquisition protocol an attempt is then made to apply all the adaptation rules in the set of rules. If the conditions of an adaptation rule are applicable then the corresponding adaptation measures are implemented, and therefore the at least one data acquisition parameter to be adapted is changed and therefore optimized. But it also follows that the larger the rule base that the medical imaging apparatus has available, the more likely it is that a data acquisition protocol can also be optimized.

In a specific example, a software update may have taken place for example in which a data acquisition parameter A could previously have two different configuration options (values) A1 and A2. With a new software version, a new configuration option A3 is introduced that promises improved image quality if the data acquisition parameter B holds the value B1. A rule for the optimization could then comprise the condition for example that the data acquisition parameter B should be B1, and the adaptation measure could comprise the action that the data acquisition parameter A is set to A3. In this regard attention is drawn to the fact that the consistency check previously employed would not change the parameter A since the value A2 continues to have validity.

In another example, a user has acquired an expanded license for software for a magnetic resonance facility. In this example, the data acquisition parameter A has three different possible values A1, A2, A3. A3 is provided with the license L1 however, which the user acquired since use of the value A3 promises an improved image quality. In an optimization of data acquisition protocols defined for equipment versions without a license, an adaptation rule can therefore include the condition that the license L1 is available, and upon this the parameter A is set to A3 as an adaptation measure.

A general expedient development of the present invention provides that in the event of an update the set of rules is obtained at least partly with the updated component and/or at least partly independently from the that component. While it is expedient for example for the set of rules to already be supplied by the manufacturer, it is also conceivable and advantageous, when an update to a new equipment version takes place, to structure sets of rules as importable and/or exportable as a whole so that sets of rules can also be supplied subsequently, for example by the manufacturer or similarly by specific application specialists who can make their knowledge about optimal use of setting options available via the set of rules.

In this regard attention should also be drawn in general terms to the aspect that the set of rules can be deposited in a domain-specific control language in the control computer and/or the memory if such a domain-specific control language (DSL—domain specific language) is present.

In another embodiment, at least one of the data acquisition protocols not defined for the current equipment version and/or at least part of the set of rules is received via a communications link, especially from a server. An explanation referring to the exchange of data acquisition protocols between different image data acquisition facilities and/or different users has already been given, where for example the server in this case can involve an Internet portal and/or a portal assigned to a medical establishment, such as a clinic or a radiology center. Import and export is possible and sensible with reference to the set of rules also, as set forth previously.

Preferably the adaptation rules of the set of rules can be defined on the basis of a user input. For example the adaptation rules can be defined by application specialists and/or employees of the manufacturer who update data acquisition protocols predefined by the manufacturer. In both cases knowledge about the best possible image quality achievable is given form in the adaptation rule and therefore also made available especially for data acquisition protocols defined by the user, which can be improved automatically in terms of the quality measure.

In another embodiment of the present invention, at least one adaptation rule of the set of rules is determined by an algorithm of artificial intelligence using machine learning and/or by an evaluation of measurement data determined by simulation and/or implementation of at least one test measurement with relevant data acquisition parameters in the adaptation rule. It is therefore also possible to determine adaptation rules at least partly automatically by using methods of artificial intelligence and/or evaluation of measurements and/or simulations in terms of the quality measure. As regards techniques of artificial intelligence, for example artificial neural networks, training data can be made available for example which gathers information on the quality measure for various combinations of data acquisition parameters, and generates relationships between data acquisition parameters which can result in optimization of the image quality.

The present invention also encompasses a medical imaging apparatus having a medical image data acquisition scanner operated by a control computer, the control computer having access to a memory in which data acquisition protocols are stored, with each data acquisition protocol containing a number of data acquisition parameters for operating the scanner, the parameters defining a data acquisition procedure. The control computer is designed or programmed in order to access the memory so as to implement any or all embodiments of the method according to the invention, as described above.

The present invention also encompasses a non-transitory, computer-readable data storage medium encoded with programming instructions that, when the storage medium is loaded into a computer or a computer system of a medical imaging apparatus having a memory in which data acquisition protocols are stored, cause the computer or computer system to operate the medical imaging apparatus in accordance with any or all embodiments of the method according to the invention, as described above.

The electronically readable data carrier can be a CD-ROM.

DESCRIPTION OF THE PREFERRED EMBODIMENTS

Figure 1:
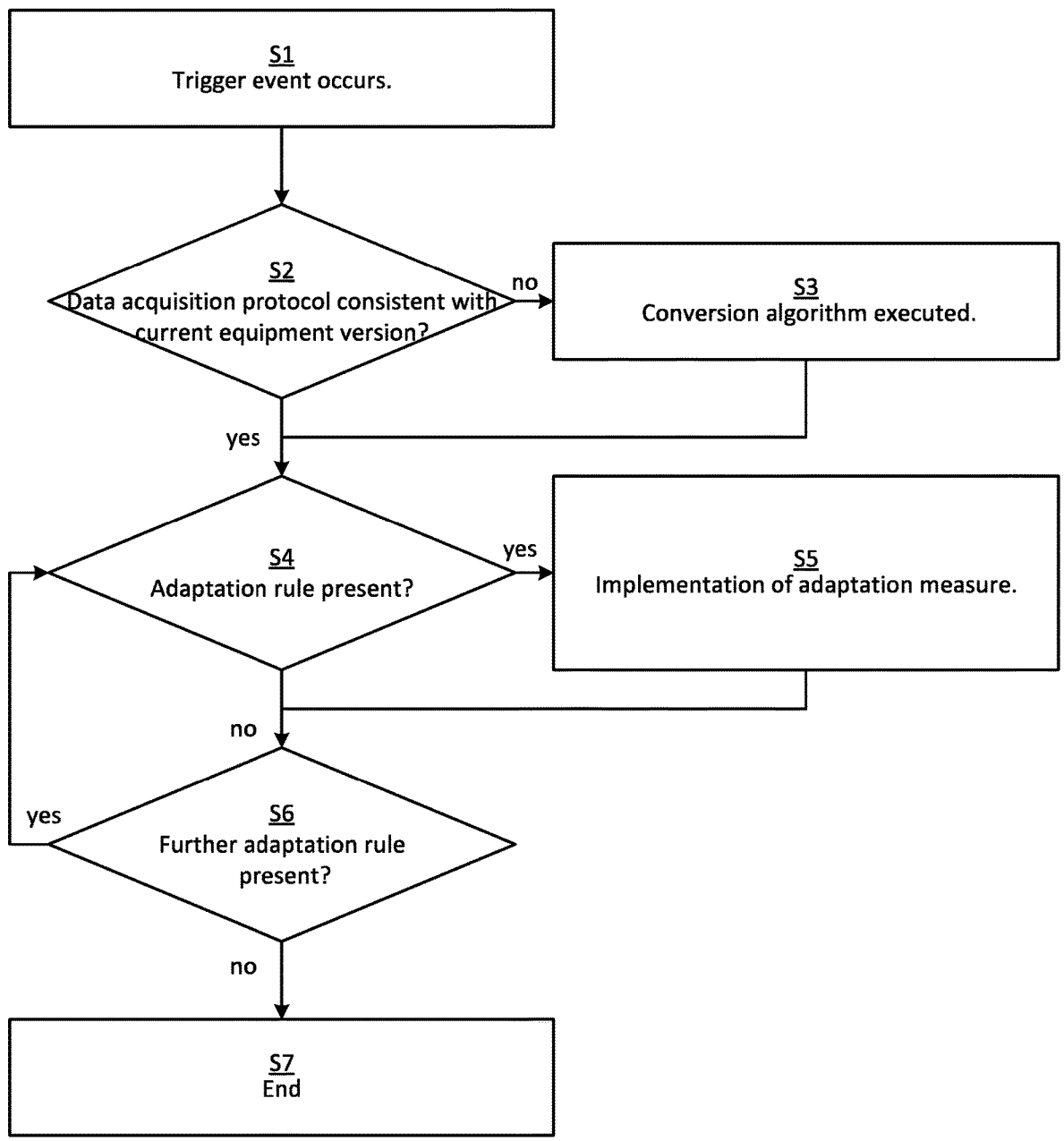
FIG. 1 is a flowchart of an exemplary embodiment of the inventive method.

FIG. 1 shows a basic flowchart of an exemplary embodiment of the inventive method. A trigger event occurs in a Step S1 that results in the conversion (if necessary) and optimization (if possible) of particular data acquisition protocols on a medical imaging apparatus, in this case a magnetic resonance apparatus. The medical imaging apparatus has a memory in which data acquisition protocols are stored. There are two types of data acquisition protocols, specifically data acquisition protocols predefined by the manufacturer, and data acquisition protocols defined by the user. Data acquisition protocols predefined by the manufacturer are made available by the manufacturer for various possible equipment versions of the magnetic resonance apparatus as far as hardware and software components are concerned. The equipment also has software licenses in the present case.

If the trigger event is therefore an update of the magnetic resonance apparatus in terms of at least one software component and/or at least one hardware component, then the data acquisition protocols to be checked for conversion and optimization are the user-defined data acquisition protocols stored in the memory, which are user-defined for an equipment version that diverges from the current equipment version. A trigger event can also be the importation of a data acquisition protocol defined for another equipment version than the current equipment version of the magnetic resonance apparatus, for example from another magnetic resonance facility via an exchange portal. The imported data acquisition protocol then needs to be checked for consistency and/or optimization options.

In a Step S2 of the method, a check is carried out as to whether the data acquisition protocol is consistent with the current equipment version. If this is not the case, a conversion algorithm is executed in a Step S3 which generates consistency and therefore removes setting options and/or data acquisition parameter combinations that are no longer permissible, and/or adapts changed data formats.

Following the conversion implemented where appropriate for consistency with the current equipment version, the data acquisition protocol is checked against various adaptation rules of a set of rules. The adaptation rules are adapted to the current equipment version, and are therefore equipment version-specific, and can already be supplied in the event of updating in terms of software and/or hardware components, or even be generally capable of being imported and exported, and can therefore be at least partly supplied subsequently and/or made available on a task-specific basis by application specialists. Adaptation rules can be based in part on user inputs and/or can be determined in part by methods of artificial intelligence and/or evaluation of measured results, but in any case aim to raise a quality measure for the image data, which measure is obtained by the data acquisition operation described by the data acquisition protocol, and which is aimed in the present case at the image quality of the image data, in this instance magnetic resonance data.

Adaptation rules comprise at least one condition and at least one adaptation measure where, in the event of the condition being fulfilled, the condition representing an evaluation of the equipment version and/or data acquisition parameters of the data acquisition protocol, the at least one adaptation measure, which adapts (or where appropriate adds) the value of at least one data acquisition parameter, is implemented. The check on the conditions takes place in a Step S4, and implementation of the adaptation measure, in the event the at least one condition being fulfilled, in a Step S5.

In a Step S6 a check is carried out as to whether further adaptation rules are present in the set of rules. If so the Step S4, and where appropriate the Step S5, is implemented again for the next adaptation rule; if all adaptation rules in the set of rules have been processed, then the method ends in a Step S7 in which data acquisition protocols that are not only consistent with the current equipment version but also optimized with reference to image quality are therefore present in the memory of the magnetic resonance facility.

In a variant of the inventive method provision can also be made in the Step S5 for the new values for the data acquisition parameters, which values result from the adaptation rule, to be initially displayed to a user, after which the said user still firstly needs to confirm the adaptation. This is optional however and can be selected as a setting by the user for example. Expediently, further information providing motivation for the user as to the change is additionally presented in the event of such a display.

Figure 2:
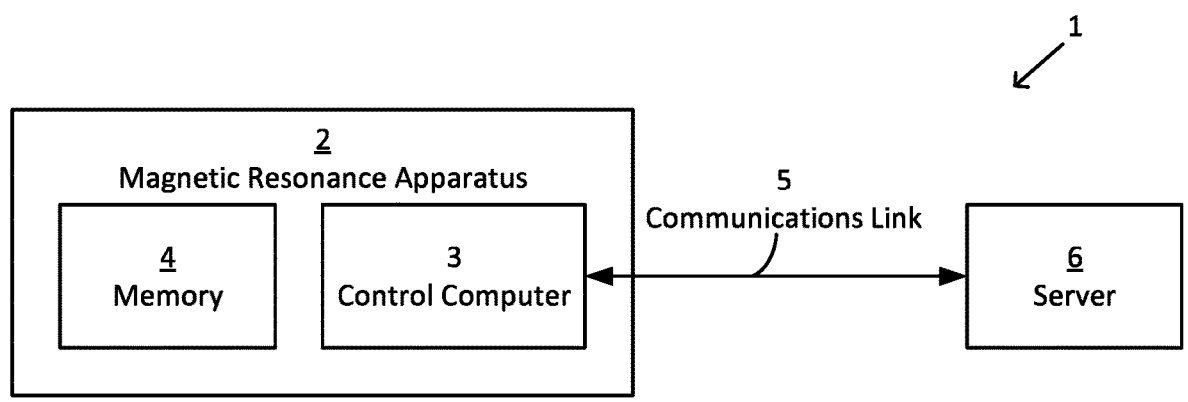
FIG. 2 schematically illustrates an inventive magnetic resonance facility.

FIG. 2 schematically illustrates a medical imaging apparatus 1, which in the present case is realized in the form of a magnetic resonance apparatus 2 where, for the sake of clarity, customary and fundamentally known components of the medical imaging apparatus 1 are omitted and just the components relevant for the present invention are represented. Operation of the medical imaging apparatus 1 is controlled by using a control computer 3 to which is assigned a memory 4, in which data acquisition protocols, and where appropriate also the set of rules, are stored. The control computer 3 is designed or programmed to implement the inventive method.

The control computer 3 communicates via a communications link 5 with at least one server 6, from which data acquisition protocols, software updates, sets of rules, and the like can be called.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for operating a medical imaging apparatus comprising a plurality of apparatus components, including software components and hardware components, and a memory in which a plurality of data acquisition protocols are stored, each stored data acquisition protocol comprising a plurality of data acquisition parameters that respectively set operation of said components of said medical imaging apparatus in order to execute the respective data acquisition protocol containing those data acquisition parameters, said method comprising:

in a computer that controls operation of said medical imaging apparatus and that has access to said memory, receiving an update input, which is at least one of an input that changes a setting scope of the data acquisition parameters of at least one of said stored data acquisition protocols to a current equipment version, and an input of a data acquisition protocol that is not defined for a current version of said medical imaging apparatus in said computer, obtaining an adaptation rule by executing an artificial intelligence algorithm using machine learning in said computer; and in said computer, treating receipt of said update input as a trigger event that causes said computer to apply an adaptation rule to all protocols not defined for said current equipment version, that modifies at least one parameter for image data acquired using the data acquisition protocol to which the adaptation rule is applied, and thereby changing contents of said memory and thereby also changing the computer in operation affecting the function of the medical imaging apparatus in accordance with the received update input.

2. A method as claimed in claim 1 comprising, in said computer, prior to applying said adaptation rule, executing a conversion algorithm that generates compatibility, with the current equipment version, of any data acquisition protocol not defined for said current equipment version.

3. A method as claimed in claim 1 comprising using said parameter selected from the group consisting of a measure that describes an image quality of an image produced from said image data, and a reduction in a data acquisition duration while maintaining a constant image quality of an image represented by said image data.

4. A method as claimed in claim 1 comprising displaying any data acquisition parameter that is to be adapted by said adaptation rule at a display screen in communication with said computer, and implementing adaptation of the displayed data acquisition parameters only upon receiving a confirmatory input into said computer after said data acquisition parameters to be adapted have been displayed at said display screen.

5. A method as claimed in claim 1 wherein the data acquisition protocol stored in said memory comprise data acquisition protocols that are predefined by a manufacturer of the medical imaging apparatus and wherein, upon receipt of said update that changes said setting scope of data acquisition parameters, also updating said data acquisition protocols that are predefined by said manufacturer.

6. A method as claimed in claim 1 comprising receiving, as said update input, a change to a license of said software components, and wherein said change of said setting scope is an addition or omission of an action performed by said software components.

7. A method as claimed in claim 1 wherein said application rule represents at least one condition that must be fulfilled for application of the adaptation rule, and an adaptation measure to be implemented upon fulfillment of said at least one condition.

8. A method as claimed in claim 7 wherein said condition evaluates at least one of said current equipment version, and at least one of said data acquisition parameters.

9. A method as claimed in claim 1 wherein, upon receipt of said update input, said computer obtains a set of rules, that includes said adaptation rule, together with said update input.

10. A method as claimed in claim 1 wherein, upon receipt of said update input, said computer obtains a set of rules, that includes said adaptation rule, independently of said update input.

11. A method as claimed in claim 1 comprising receiving said update input in said computer, which imports a data acquisition protocol not defined for the current equipment version, by communication between said computer and a server.

12. A method as claimed in claim 1 comprising, together with said update input, receiving an input, by communication between said computer and a server, into said computer of a set of rules that includes said adaptation rule.

13. A method as claimed in claim 1 comprising determining said at least one adaptation rule in said computer by evaluating measurement data from a simulation of operation of said medical imaging apparatus executed in said computer.

14. A method as claimed in claim 1 comprising determining said at least one adaptation rule in said computer by operating said medical imaging apparatus in order to implement at least one test measurement with data acquisition parameters that are relevant to said at least one adaptation rule.

15. A medical imaging apparatus comprising:
a plurality of apparatus components, including software components and hardware components;
a memory in which a plurality of data acquisition protocols are stored, each stored data acquisition protocol comprising a plurality of data acquisition parameters that respectively set operation of said components of said medical imaging apparatus in order to execute the respective data acquisition protocol containing those data acquisition parameters;
a computer configured to control operation of said components of said medical imaging apparatus and that has access to said memory, said computer being configured to receive an update input, which is at least one of an input that changes a setting scope of the data acquisition parameters of at least one of said stored data acquisition protocols to a current equipment version, and an input of a data acquisition protocol that is not defined for a current version of said medical imaging apparatus said computer configured to obtain an adaptation rule by executing an artificial intelligence algorithm using machine learning in said computer; and
said computer being configured to treat receipt of said update input as a trigger event that causes said computer to apply an adaptation rule to all protocols not defined for said current equipment version, that modifies at least one parameter for image data acquired using the data acquisition protocol to which the adaptation rule is applied, and thereby to change contents of said memory and thereby also to change the computer in operation affecting the function of the medical imaging apparatus in accordance with the received update input.

16. A non-transitory, computer-readable data storage medium encoded with programming instructions for operating a medical imaging apparatus comprising a plurality of apparatus components, including software components and hardware components, and a memory in which a plurality of data acquisition protocols are stored, each stored data acquisition protocol comprising a plurality of data acquisition parameters that respectively set operation of said components of said medical imaging apparatus in order to execute the respective data acquisition protocol containing those data acquisition parameters, and a computer that controls operation of said medical imaging apparatus and that has access to said memory, said programming instructions causing said computer to:
receive an update input, which is at least one of an input that changes a setting scope of the data acquisition parameters of at least one of said stored data acquisition protocols to a current equipment version, and an input of a data acquisition protocol that is not defined for a current version of said medical imaging apparatus obtain an adaptation rule by executing an artificial intelligence algorithm using machine learning in said computer; and
treat receipt of said update input as a trigger event that causes said computer to apply an adaptation rule to all protocols not defined for said current equipment version, that modifies at least one parameter for image data acquired using the data acquisition protocol to which the adaptation rule is applied, and thereby change contents of said memory and thereby also change the computer in operation affecting the function of the medical imaging apparatus in accordance with the received update input.

* * * * *